(12) United States Patent
Brown et al.

(10) Patent No.: US 7,153,538 B2
(45) Date of Patent: Dec. 26, 2006

(54) METHOD AND APPARATUS FOR THE COATING OF SUBSTRATES FOR PHARMACEUTICAL USE

(75) Inventors: Steven R. Brown, Kent (GB); Linda A. Reeves, Kent (GB); John N. Staniforth, Bath (GB)

(73) Assignee: Phoqus Pharmaceuticals Limited, West Malling (GB)

( * ) Notice: Subject to any disclaimer, the term of this patent is extended or adjusted under 35 U.S.C. 154(b) by 294 days.

(21) Appl. No.: 09/962,624

(22) Filed: Sep. 26, 2001

(65) Prior Publication Data

US 2002/0197388 A1    Dec. 26, 2002

Related U.S. Application Data

(63) Continuation of application No. 09/310,741, filed on May 13, 1999, now abandoned.

(30) Foreign Application Priority Data

Nov. 13, 1996  (GB)  .................. 9623634.4
Nov. 13, 1997  (GB)  ..................... PCT/GB97/03121

(51) Int. Cl.
*B05D 1/04*    (2006.01)

(52) U.S. Cl. ................. 427/2.14; 427/2.21; 427/469; 427/470; 427/475; 427/485

(58) Field of Classification Search ............... 427/2.14, 427/2.21, 265, 469, 470, 483, 458, 415, 475, 427/485

See application file for complete search history.

(56) References Cited

U.S. PATENT DOCUMENTS

| | | | |
|---|---|---|---|
| 2,698,814 A | 1/1955 | Ransburg | |
| 3,764,538 A | 10/1973 | Shelffo | ............ 430/109 |
| 3,900,000 A | 8/1975 | Gallen | |
| 4,029,757 A | 6/1977 | Mlodozeniec et al. | |
| 4,128,445 A | 12/1978 | Sturzenegger et al. | |
| 4,176,175 A | 11/1979 | Maekawa et al. | ............ 424/35 |
| 4,197,289 A * | 4/1980 | Sturzenegger et al. | ...... 424/443 |
| 4,201,834 A | 5/1980 | Hannon et al. | |
| 4,322,449 A | 3/1982 | Voss et al. | |
| 4,349,531 A | 9/1982 | Mlodozeniec et al. | ........ 424/27 |
| 4,359,483 A | 11/1982 | Kaetsu et al. | |
| 4,427,712 A | 1/1984 | Pan | ............ 427/13 |
| 4,433,076 A | 2/1984 | Bauer et al. | ................ 523/342 |
| 4,454,125 A | 6/1984 | Demopoulos | |
| 4,482,387 A | 11/1984 | Wood et al. | |
| RE31,764 E | 12/1984 | Voss et al. | |
| 4,547,571 A | 10/1985 | Mukohyama et al. | ......... 536/90 |

(Continued)

FOREIGN PATENT DOCUMENTS

DE    2 247 701    4/1974

(Continued)

OTHER PUBLICATIONS

Bocchi, G.J., "Powder Coating The Complete Finishers Handbook"; Published by the Powder Coating Institute; pp. 1-7;(1994).

(Continued)

*Primary Examiner*—Fred J. Parker
(74) *Attorney, Agent, or Firm*—Nixon & Vanderhye

(57) ABSTRACT

A method of coating a pharmaceutical substrate includes the steps of applying an active coating material to a surface of the substrate to form an active coating layer and applying a cover coating material onto the active coating layer to form a cover coating layer. The active coating layer is substantially completely covered by the cover coating layer.

65 Claims, 3 Drawing Sheets

U.S. PATENT DOCUMENTS

| | | | |
|---|---|---|---|
| 4,548,825 A | 10/1985 | Voss et al. | |
| 4,704,295 A | 11/1987 | Porter et al. | 424/440 |
| 4,786,505 A | 11/1988 | Lovgren et al. | |
| 4,800,079 A | 1/1989 | Boyer | |
| 4,810,501 A | 3/1989 | Ghebre-Sellassie et al. | |
| 4,828,840 A | 5/1989 | Sakamoto et al. | |
| 4,925,670 A | 5/1990 | Schmidt | 424/443 |
| 4,935,246 A | 6/1990 | Ahrens | |
| 4,994,273 A | 2/1991 | Zentner et al. | |
| 5,011,694 A | 4/1991 | Nuernberg et al. | |
| 5,076,706 A | 12/1991 | Shibuya et al. | |
| 5,206,030 A | 4/1993 | Wheatley et al. | 424/490 |
| 5,320,796 A | 6/1994 | Harashima et al. | |
| 5,411,730 A | 5/1995 | Kiroptin et al. | |
| 5,436,026 A | 7/1995 | Berta | |
| 5,470,603 A * | 11/1995 | Staniforth et al. | 427/2.14 |
| 5,474,786 A * | 12/1995 | Kotwal et al. | 424/472 |
| 5,540,995 A | 7/1996 | Kitano et al. | |
| 5,615,614 A | 4/1997 | Van Pelt | 101/488 |
| 5,699,649 A | 12/1997 | Abrams et al. | 53/428 |
| 5,714,007 A | 2/1998 | Pletcher et al. | |
| 5,792,513 A | 8/1998 | Koslow et al. | |
| 5,846,595 A * | 12/1998 | Sun et al. | 427/2.14 |
| 5,857,456 A | 1/1999 | Sun et al. | |
| 6,026,809 A | 2/2000 | Abrams et al. | |
| 6,074,688 A | 6/2000 | Pletcher et al. | |
| 6,117,479 A | 9/2000 | Hogan et al. | |
| 6,294,024 B1 | 9/2001 | Sun et al. | |
| 6,298,847 B1 | 10/2001 | Datta et al. | |
| 2001/0018098 A1 | 8/2001 | Pletcher et al. | |

FOREIGN PATENT DOCUMENTS

| | | |
|---|---|---|
| DE | 31 06984 A1 | 2/1982 |
| DE | 3 049 179 A1 | 7/1982 |
| DE | 30 49 179 A1 | 7/1982 |
| EP | 0 011 268 B1 | 5/1980 |
| EP | 0 020 181 A1 | 12/1980 |
| EP | 0 063 014 | 10/1982 |
| EP | 0 107 557 A1 | 5/1984 |
| EP | 0 164 959 | 12/1985 |
| EP | 0 164 959 A2 | 12/1985 |
| EP | 0 220 670 A2 | 5/1987 |
| EP | 0 259 749 A1 | 3/1988 |
| EP | 0 277 741 A1 | 8/1988 |
| EP | 0 277 741 B1 | 8/1988 |
| EP | 0 277 741 A | 10/1988 |
| EP | 0 307 642 | 3/1989 |
| EP | 0 307 642 A2 | 3/1989 |
| EP | 0 452 862 A2 | 10/1991 |
| EP | 0 459 048 B1 | 12/1991 |
| EP | 0 536 791 B1 | 4/1993 |
| EP | 0 543 541 A1 | 5/1993 |
| EP | 0 551 700 A1 | 7/1993 |
| EP | 0 551 700 A2 | 7/1993 |
| EP | 0 567 201 A2 | 10/1993 |
| EP | 0 567 201 B1 | 10/1993 |
| EP | 0 607 009 A1 | 7/1994 |
| EP | 0 607 009 B1 | 7/1994 |
| EP | 0 661 091 B1 | 7/1995 |
| EP | 0 678 561 A2 | 10/1995 |
| EP | 0 678 564 B1 | 10/1995 |
| FR | D 24 084 | 11/1966 |
| GB | 1075404 | 7/1967 |
| GB | 1108837 | 4/1968 |
| GB | 1 561 100 | 2/1980 |
| GB | 561 100 | 2/1980 |
| GB | 2 056 885 A | 3/1981 |
| GB | 2 065 691 A | 7/1981 |
| GB | 2 179 254 | 3/1987 |
| GB | 2 203 336 A | 10/1988 |
| GB | 2 241 889 A | 9/1991 |
| GB | 2 253 164 * | 2/1992 |
| GB | 2 253 164 A | 9/1992 |
| GB | 2 253 164 B | 10/1994 |
| LU | 52 460 | 6/1968 |
| LU | 52 460 A | 6/1968 |
| WO | 91/16041 | 10/1991 |
| WO | 92/11002 | 7/1992 |
| WO | 92/14451 | 9/1992 |
| WO | WO 92/14451 | 9/1992 |
| WO | 94/05263 | 3/1994 |
| WO | 94/11446 | 5/1994 |
| WO | 96/02236 | 2/1996 |
| WO | 96/11707 | 4/1996 |
| WO | 96/35413 | 11/1996 |
| WO | WO 96/35413 * | 11/1996 |
| WO | WO 96/35516 | 11/1996 |
| WO | 96/39256 | 12/1996 |
| WO | 96/39257 | 12/1996 |
| WO | 97/04827 | 2/1997 |
| WO | 97/37775 | 10/1997 |
| WO | 97/37803 | 10/1997 |
| WO | 97/38480 | 10/1997 |
| WO | 97/47346 | 12/1997 |
| WO | 97/47347 | 12/1997 |
| WO | 99/06593 | 2/1999 |
| WO | 99/06814 | 2/1999 |
| WO | 99/13817 | 3/1999 |

OTHER PUBLICATIONS

PCT/GB96/01101, International Search Report, Sep. 5, 1996, 4 pgs.
PCT/GB96/01101, International Preliminary Examination Report, Aug. 18, 1997, 11 pgs.
Examination Report under Section 18(3), Application No. GB 9723708.5 dated May 27, 1998, 4 pgs.
EP Official Action, Application No. 96 913 629 0-2114, dated Oct. 11, 1999, 2 pgs.
EP Official Action, Application No. 96 913 629 0-2114, dated Jan. 25, 2001, 3 pgs.
Canadian Intellectual Property Office Official Action, Application No. 2,220,506, dated Feb. 17, 2005, 4 pgs.
EP Combined Search Report and Examination Report under Sections 17 and 18(3), Application No. GB 9828580.2, dated Feb. 4, 1999, 2 pgs.
EP Communication pursuant to Article 96(2) EPC, Application No. 00 117 256.8-2108, dated May 5, 2003, 3 pgs.
EP Communication pursuant to Article 96(2) EPC, Application No. 00 117 256.8-2108, dated Apr. 8, 2005, 3 pgs.
Eschborn/Tanus; Pharmazeutische Stoffliste 13. Auflage; List of Pharmaceutical Substances 13$^{th}$ Edition; *Bearbeitet und herausgegeben von Prepared and published by Pharma-Daten-Service*; pp. 230-231, (Sep. 2003).
Chemical Abstracts, vol. 120, No. 20, (1994), Grosvenor M.P. Diss. Abstr. Int., vol. 53, No. 7 (1991) Bath, p. 3492, Grosvenor M.P.
Kirk-Othmer Encyclopedia of Chemical Technology, vol. 19, 3rd Ed., p. 1-2 (1982).
EP Communication pursuant to Article 96(2) EPC, Application No. 97 912 341.1-2114, dated Jan. 24, 2002, 3 pgs.
EP Examination Report under Section 18(3), Application No. GB 9911055.3, dated Sep. 28, 2000, 3 pgs.
EP Combined Search Report and Examination Report under Sections 17 and 18(3), Application No. GB 0103413.1, dated Apr. 17, 2001, 2 pgs.
Canadian Intellectual Property Office Official Action, Application No. 2,279,841, dated Dec. 13, 2004, 3 pgs.
International Preliminary Examination Report, International Application No. PCT/GB97/03121, dated Feb. 12, 1999.
Kirk-Othmer, Encyclopedia of Chemical Technology, Third Edition, vol. 19; "Powder Coatings to Recycling", 4 pgs.
EP Communicatoin pursuant to Article 96(2) EPC, Application No. 01 948 995.4—1214, dated Dec. 6, 2004, 3 pgs.

EP Communication pursuant to Article 96(2) EPC, Applicatoin No. 01 948 995.4—1214, dated Jun. 26, 2003, 3 pgs.
EP Examination Report under Section 18(3), Application No. GB 0217155.1, dated Dec. 5, 2003, 3 pgs.

Interntional Preliminary Examination Report, Int'l Application No. PCT/GB01/00425, dated Jun. 6, 2002, 17 pgs.

* cited by examiner

METHOD AND APPARATUS FOR THE COATING OF SUBSTRATES FOR PHARMACEUTICAL USE

This application is a continuation of application Ser. No. 09/310,741, filed May 13, 1999, abandoned, the entire content of which is hereby incorporated by reference in this application.

The present invention relates to methods of coating substrates, to apparatus for coating substrates and to coated substrates for pharmaceutical use. In particular, but not exclusively, the invention relates to the coating of pharmaceutical substrates to produce solid dosage forms.

It is to be understood that the term "solid dosage form" is to be interpreted in a broad sense as covering a wide variety of pharmaceutical products. Thus the term covers pharmaceutical products to be taken orally, for example, pharmaceutical tablets of conventional shape as well as capsules and spherules and tablets of unconventional shape. It will be understood that the pharmaceutical substrate may be a conventional tablet core or may be for example an edible sheet or film. The term also covers pharmaceutical products not taken orally, for example, a pessary, a bougie, a suppository or a patch for application to the skin. Also, where reference is made to "pharmaceutical substrate" it is to be understood that the term covers the substrates of the solid dosage forms indicated above. The term "solid dosage form" does not, however, include pharmaceutical products such as small pellets and granules, for example small pellets which are filled into capsule shells for administration and granules which are compressed to form tablets. Such pellets or granules are not themselves each solid dosage forms but rather, when combined together in a capsule or tablet, define in combination a solid dosage form.

The invention is of particular application to pharmaceutical tablets of conventional shape. Where reference is made throughout the specification to pharmaceutical tablets, it should be understood that this should be interpreted in a broad sense, unless it is clear to the contrary, as covering also other pharmaceutical products taken orally, for example capsules and spherules.

It will be understood that the term "active material" and "active component" used throughout the specification includes material which is biologically active and will comprise one or a mixture of pharmaceutical materials. The pharmaceutical materials include those materials which are administered for the prevention and/or treatment of disease.

BACKGROUND OF THE INVENTION

In a conventional method of producing a pharmaceutical tablet, a mixture containing the biologically active ingredient together with diluents such as lactose and other ingredients is mixed and portions of the mixture are formed into discrete tablets by, for example, pressing samples of the mixture.

The resulting tablet core may be coated using, for example, a conventional liquid coating technique in which the tablet cores are tumbled in a drum while liquid coating material is sprayed onto the surfaces of the tablet cores. The liquid coating on the surfaces of the cores is usually dried by heating to dry the coating.

A problem with the method of producing tablets described above is that, due to inhomogeneity of the mixture from which the tablet cores are made, the amount of active ingredient in the resulting tablet cores varies from one tablet to the next. While that is a problem for all types of tablet core produced in that way, it is a particularly serious problem when the amount of active ingredient in each core is low, for example for active compounds of high activity. In that case a small absolute variation in the percentage amount of active ingredient in the cores corresponds to a significant variation in the dose contained in each tablet which is clearly most undesirable.

Various solutions to that problem have been proposed.

In one method, the active ingredient and a small amount of diluent are granulated together and the granulated mixture is added to further diluent. The mixture is then compressed in the usual way to form tablet cores. Using that method, at each stage the proportion of active ingredient added to the diluent is high thus helping to reduce the variation in the dose in each tablet core. However, the variation in the dose for tablets formed by this method is still found to be as much as ±15%.

In an alternative known method, a two-layer tablet core is produced by compressing a powder having a lower layer of diluent and an upper layer of diluent mixed with the active ingredient. Cores formed by this method, however, require special designs of presses and are found to have a relatively large variation in their contained dose. They also require reformulation of the components making up the core. Also, such presses generally have lower rates of production of cores than standard presses.

In another known method, a coating solution containing active material is applied to the surfaces of small beads using conventional spray coating techniques, for example by spraying the coating solution towards the beads as they are tumbled in a revolving drum. The coated beads are filled into capsule shells for administration. Such a method is not appropriate for use where accuracy in the amount of the active material applied to the cores is required because there is little control over the amount of coating material applied to each core using that method.

SUMMARY OF THE INVENTION

It is an object of the invention to overcome or mitigate one or more of the above mentioned disadvantages.

According to the invention, there is provided a method of coating a pharmaceutical substrate, the method including the steps of:

(a) applying an active coating material to a surface of the substrate to form an active coating layer, the active coating material comprising biologically active material and (b) applying a cover coating material onto the active coating layer to form a cover coating layer such that the active coating layer is substantially completely covered by the cover coating layer.

Thus biologically active material is applied to the outer surface of the substrate. In the case of pharmaceutical tablets, active material is applied to an outer surface of a preformed pharmaceutical tablet core. The active coating material may therefore be applied to the substrate in a small quantity and thus the percentage of biologically active component in the active coating material mixture may be high, leading to less variation in the amount of active material from one dosage form to the next compared with the known methods described above.

The active coating material may be applied to a substrate which contains no biologically active material or may be applied to a substrate which contains the same or a different biologically active material. Thus the method may be used to provide a solid dosage form which contains one active component in the substrate and a different active component as a coating on the surface of the substrate. It is envisaged that those active components could be released at different rates.

The active material may be applied to a substrate to which one or more coating layers have already been applied. For example, where the substrate is a tablet core containing active material, the core may be coated with a delayed release coating prior to the application of the active coating material.

Where the material containing active components is applied to the outer surfaces of a pharmaceutical substrate as a coating, the layer containing the active components will be susceptible to damage resulting in loss of active material. By applying a cover coating over the surface of the active coating layer the active coating layer is protected from damage. That protection is especially desirable when the coating material contains a small amount of active component. In addition to protection from physical damage, the coating may also provide protection from chemical damage; for example, the cover coating may be moisture resistant and/or may give delayed release of the active components.

It is clearly preferable for the cover coating to cover completely all of the active coating but incomplete coating, for example at the edge of the active coating layer, may be tolerated in some circumstances.

While the cover coating will often comprise a single coating of one material composition, it may comprise more than one coating and/or coatings including more than one composition.

The cover coating may comprise a preformed sheet or film which is applied over the active coating.

Preferably, the active coating material is applied electrostatically. There are various advantages in applying coating materials electrostatically, for example, reduction in waste of coating material, improved coating efficiency and improved coating weight uniformity.

In one alternative embodiment of the invention, the active coating material is applied in the form of a dry powder.

Advantageously, at least 90% by weight of the particles of the active coating material have a particle size not more than 200 μm.

Advantageously, at least 90% by weight of the particles of the active coating material have a particle size between from 1 to 200 μm. Preferably, at least 90% by weight of the particles of the active coating material have a particle size between from 1 μm to 100 μm. The term "particle size" refers to the equivalent particle diameter of the particles and may be measured using, for example, laser light diffraction. The particle size of the powder is an important factor in powder coating techniques. If the particles of the powder are very small, the powder will often be too cohesive for successful powder application using many powder coating techniques. However, large particles can be disadvantageous because they are often more difficult to coat onto a surface and, if the coating material is to be fused after application to the surface, longer fusing times may be required, leading to increased risk of damage to the substrate and to the active component.

Where reference is made to % by weight of particles, for example the % by weight of particles having a particular size, the particles will also preferably have that % by volume of particles of that size.

Alternatively, the coating material may be applied in the form of a liquid.

Advantageously, the method includes the step of applying a metered dose of the active coating material to a surface of the substrate.

In conventional coating methods, the part to be coated, for example, a pharmaceutical tablet core, is tumbled in a revolving drum while coating material is sprayed into the drum such that coating material is applied to all of the surfaces of the cores. It has been proposed that the substrate may be supported on a surface while coating material is sprayed towards exposed surfaces of the substrate. A problem with such methods is that there is a large variation in the amount of coating material applied to each core. While that can be tolerated where the coating is, for example, a cosmetic coat, where the coating material contains active material, very accurate application of the coating material on each surface is required.

Advantageously, a metered dose of coating material is applied to each substrate, thus allowing for the application of the required amount of active material to each substrate. This is to be contrasted with the known methods where coating material is sprayed towards the cores. In that case the amount of coating material applied to each substrate depends on many factors all of which would require close control if accurate application is to be achieved. It will be understood that whilst reference is made to applying a metered dose, that should not be taken to imply that there is necessarily any measurement of the amount of material applied.

The active coating material may be applied in the form of a jet of particles of coating material Advantageously, the active coating material is applied in the form of a liquid. Thus a metered volume of liquid may be applied to each substrate.

Advantageously, the active coating material is applied in the form of individual liquid droplets which are propelled from the supply directly towards a surface of the substrate.

Where the material is applied as a plurality of individual droplets, it is more simple to alter the dose of active material applied to the substrate by changing the number of droplets applied. Thus advantageously, the number of droplets applied is controllable.

Advantageously, substantially all of the active coating material released from the supply is applied to a surface of a substrate. It is highly preferable for there to be little or no overspray of the coating material.

Advantageously, a predetermined number of droplets of active coating material are applied to the surface of the substrate. Thus where the droplets are of the same size, the number of droplets applied to the substrate surface determines the amount of active material applied. By altering the number of droplets applied, the apparatus used can easily be adapted to apply the required quantity of active material.

Advantageously, the coating material is applied in the form of a jet of liquid droplets directed at an exposed surface of the substrate. Whereas known spray devices for use in coating processes spray a wide area with coating material, a jet of liquid droplets allows material to be applied more accurately with less over-spray.

Advantageously, the method is such that the coefficient of variation of the quantity of active coating material applied to each substrate (or region of the substrate) is not more than 15%.

As indicated above, where the coating material includes active material, the accuracy and reproducibility of the application of the material to the substrates is of particular importance. For known spraying techniques such as those described above, the coefficient of variation can be 50% or more. Whilst that is acceptable where the coating is a cosmetic coating, it is not acceptable where the coating contains active material. Preferably the coefficient of variation is not more than 10%, and most preferably 3% or less.

Advantageously, an ink jet head is used to apply coating material to the substrate. A conventional ink jet head, for example those used for ink jet printers, can be used to apply an easily controllable amount of material from the head onto a substrate.

Advantageously the active coating material is applied to only a part of the surface of the substrate.

Advantageously, the area of the surface of the substrate covered by the active coating layer is less than 40% of the total surface area of the substrate. Advantageously, the area covered by the active coating layer is less than 25% of the total surface area of the substrate. The active coating may form a plurality of small coated regions on the surface of the substrate.

Advantageously, the active coating layer covers only a part of the exposed surface of the substrate. The area of the exposed surface covered by the active coating layer may be less than 10% of the total area of the exposed surface.

Where the quantity of active material to be administered using each solid dose is small, as indicated above, it is advantageous for the proportion of active component in the active coating material to be large.

In conventional coating methods the part to be coated, for example a pharmaceutical tablet core, is tumbled in a revolving drum during the coating process such that coating material is applied to all of the surfaces of the core.

By using the method described above, a smaller proportion of the surface of the substrate is covered and therefore a smaller amount of coating material may be used. Thus the proportion of active component in the coating material is increased.

Another problem with the known methods described above is that there is overspray of coating material which has to be discarded or recycled. That would be particularly disadvantageous in a method according to the present invention in which the coating material contains an active component.

Using the method described above, coating material may be applied accurately to a predetermined part of the substrate, thereby helping to reduce loss of powder due to overspray.

Advantageously, the area of the surface covered by the active coating layer is less than 25%, preferably less than 10% of the total area of the surface. Preferably, the coated area is less than 5% of the total area. The active coating material may be applied to the surface of the substrate in the form of a small spot.

Advantageously, the cover coating is applied to only a part of the surface of the substrate. Thus, as described below, where the substrate is a pharmaceutical tablet core, the cover coating material may be applied to one face only of the tablet core.

The cover coating may cover only a part of the exposed surface of the substrate.

Advantageously, the active coating material further includes one or more excipients. The formulation will usually consist of the active component and a mixture of excipients that will aid in the coating of the material. The formulation may also include other components, for example, colorants and/or flavourings and/or agents to control the rate of release of the active component.

Advantageously, the substrate is supported on a support means during the coating of the active coating material. This is particularly advantageous where the substrate is fragile, for example a tablet core, because the likelihood of damage to the substrate is reduced. Supporting of the substrate also allows the application of the coating material to be more accurate and the uniformity of coating can be improved compared with the case in which the substrate is, for example, tumbled in a revolving drum during the coating stage, as is conventional practice for the coating of tablet cores.

Advantageously, the support means conveys the substrate through a region adjacent to a source of the active coating material. That allows the method to be continuous.

In one advantageous embodiment of the invention, the method comprises supporting the substrate adjacent to the source of the active coating material with a surface of the substrate maintained at such a different electric potential from that of the active coating material that the application of the electric potential causes the active coating material to move from the source of the active coating material towards the substrate, a surface of the substrate becoming coated with the active coating material.

Preferably, the substrate is supported from above and the powder moves from the source upwards towards a lower surface of the substrate.

Preferably, the substrate is charged when the substrate is adjacent the source of the active coating material. Alternatively, or in addition, the source of active coating material may be charged.

The method may further include the step that after the active coating layer is applied the active coating material is treated to form an active film coating secured to the surface of the substrate. Where the coating material is in the form of a powder material, the treatment advantageously comprises a heating step, preferably by infra red radiation, but other forms of electromagnetic radiation may be used. Usually, the change in the coating upon heating will simply be a physical change from a powder to a liquid and then, on cooling, to a solid coating, but there are other possibilities: for example, the powder coating may comprise a polymer which is cured during the treatment step, for example by irradiation with energy in the gamma, ultra violet or radio frequency bands, to form a cross-linked polymer coating.

Alternatively, the active coating material applied to the surface of the substrate might not be treated to form an active film coating. A cover coating applied subsequently over the active coating material could be used to seal the active coating on the surface of the substrate.

Where the coating material is in the form of a liquid, the treatment advantageously comprises drying the coating material with a heater although other methods could be used.

The coating material containing the active component is susceptible to damage at high temperatures and it is therefore particularly important that the temperature of treatment is not high. Advantageously, the temperature of treatment is less than 250° C., preferably less than 200° C. and more preferably less than 150° C. Where the higher treatment temperatures are used, the duration of the treatment is advantageously short to reduce the possibility of damage of the coating material.

Preferably, the cover coating material is applied electrostatically. The cover coating material may be in the form of a powder. The cover coating material may also include active material. The active material in the cover coating may be the same or different from the active material in the active coating layer.

Advantageously, at least 90% by weight of the particles of the cover coating material have a particle size not more than 200 µm, preferably between from 1 to 200 µm.

Advantageously, the substrate is supported on a support means during the coating of the cover coating material. As indicated above, that reduces the risk of damage of the substrate and can increase the accuracy of the application of the coating.

Preferably, the support means conveys the substrate through a region adjacent to a source of the cover coating material.

In one advantageous embodiment of the invention, the method comprises supporting the substrate adjacent to the source of the cover coating material with a surface of the substrate maintained at such a different electric potential from that of the cover coating material that the application of the electric potential causes the cover coating material to move from the source of the cover coating material towards the substrate, a surface of the substrate becoming coated with the cover coating material.

Advantageously, the substrate is supported from above and the powder moves from the source upwards towards a lower surface of the substrate.

Preferably, the substrate is charged when the substrate is adjacent to the source of the cover coating material. Alternatively, or in addition, the source of cover coating material may be charged.

Advantageously, the method further includes the step that after the cover coating layer is applied the cover coating material is treated to form a film coating secured to the surface of the substrate. The treatment of the cover coating layer may be similar to that of the active coating layer described above.

As indicated above, in a preferred embodiment of the invention the active coating layer covers only part of a surface of the substrate. In that embodiment, the cover coating layer may cover only part of a surface of the substrate. The cover coating layer may cover the whole surface of the substrate.

The cover coating may comprise a preformed sheet or film which is applied over the active coating layer.

The method may further include the step of applying a further coating material to a surface of the substrate to form a further coating layer. The further coating material may include biologically active material, the further coating layer forming a further active coating layer and the method may further include the step of applying a further cover coating material onto the further active coating layer to form a further cover coating layer such that the further active coating layer is substantially completely covered by the further cover coating layer.

Thus substrates having two or more different active components may be produced. The cover coating material covering the first active coating may be different from that covering the second active coating so that the rate of release of the first active component may be different from that of the second active component. Alternatively, the two active components may be the same and the cover coatings may be the same or different materials. One or more of the cover coating materials may contain active material.

Advantageously, the method is continuous. In practice, there are considerable advantages in being able to operate the coating process continuously rather than as a batch process.

Advantageously, the coated pharmaceutical substrate is a solid dosage form, preferably a solid dosage form for oral administration.

Where reference is made to the quantity of active coating material being substantially equal to a dose of the active material, it will be understood that the quantity of one dose may be a fraction of the single standard dose, for example ½ or ⅓ of a single standard dose of the active material. It will be understood that the quantity of active material will depend on the active component used and the number of solid dosage forms to be taken by the patient for each dose. Where more than one layer of the active coating material is to be applied to each substrate, the quantity of active component in each layer will be chosen accordingly.

For example, where the active material is applied to the surface of a conventional tablet core, the amount of active material applied to each core will usually contain one dose of the active component.

Where the substrate is other than a conventional tablet core, for example where the substrate is in the form of a film or sheet, a plurality of regions of active coating material may be applied to the surface of the substrate.

The amount of active coating material applied to each region may be chosen so as to contain substantially one dose of the active component. In that embodiment, the method advantageously further includes the step of dividing the coated substrate to form a plurality of solid dosage forms. In the example described above, each solid dosage form would include substantially one dose of the active material. The cover coating may be applied before the coated substrate is divided. Alternatively, the cover coating may be applied after the dividing step.

The invention also provides a method of coating a substrate, the method comprising applying an active coating material to a surface of the substrate to form an active coating layer, the active coating material comprising biologically active material, applying a cover coating layer over the exposed surfaces of the active coating layer and dividing the layered product to form layered portions, each layered portion including substantially one dose of the active material.

A particularly preferred embodiment of the invention provides a method of coating a substrate, the method comprising applying an active powder material to a surface of the substrate to form an active coating layer, the active coating material comprising biologically active material and being applied electrostatically to the surface of the substrate, and applying a cover coating over the exposed surfaces of the active coating layer to substantially completely cover the active coating layer on the surface of the substrate.

It will be appreciated that once the cover coating layer has been applied over the exposed surfaces of the active coating layer, a further coating layer may be applied such that the final product is substantially completely coated.

For example, where the substrate is a pharmaceutical tablet core, the active coating layer and cover coating layer may be applied to one face of the tablet core. the partially coated core may subsequently have a further coating applied to the uncoated surfaces of the core.

Advantageously, the substrate is moved relative to a source of active coating material during the application of the active coating layer to the substrate.

The invention also provides apparatus for coating a pharmaceutical substrate according to a method as described above.

The invention also provides an apparatus for coating a pharmaceutical substrate, the apparatus comprising:

(a) a source of active coating material, (b) support means for supporting a substrate adjacent to the source of the active coating material such that the active coating material forms an active coating layer on a surface of the substrate, (c) a source of a cover coating material, (d) means for conveying the substrate having the active coating layer to a position adjacent to the source of cover coating material such that the cover coating material forms a cover coating layer which substantially completely covers the active coating layer.

The apparatus advantageously includes means for applying the active coating material and/or the cover coating material electrostatically. As indicated above, the coating material may be applied in the form of a dry powder or in the form of a liquid.

Advantageously, the source of active coating material comprises a conveyor for conveying active coating material through a region in which the substrate is supported by the support means.

The conveyor may comprise a conveyor belt. Where the conveyor is used it is possible to provide a substantially uniform supply of coating material to the region in which the coating is applied.

Advantageously the apparatus further includes means for supplying active coating material to the source, comprising a reservoir of active coating material arranged adjacent to the conveyor, and means for transferring the active coating material from the reservoir to the conveyor. The rate of transfer of the coating material from the reservoir to the conveyor can be adjusted to change the amount of coating material applied to the substrate.

Advantageously, the means for transferring the active coating material includes charging means for applying a charge to the conveyor. The charge may be applied using a corona charge wire adjacent to the conveyor. The charged conveyor attracts coating material from the reservoir onto the surface of the conveyor from where it is conveyed to the region in which the coating is applied. Thus it is possible to obtain a very thin uniform layer of coating material on the conveyor surface.

Preferably, the reservoir is arranged below the conveyor.

Advantageously, the source comprises means for applying a metered dose of active coating material on a surface of the substrate. The source may comprise an ink jet head.

The source may comprise means for directing droplets of liquid active coating material towards a surface of the substrate.

The apparatus may comprise means for applying active coating material from the source onto only a part of the surface of the substrate.

The means for applying the coating material may include means for directing coating material towards the surface of the substrate in the form of a jet of liquid droplets. The means for forming a jet of liquid droplets may be similar to devices known in the field of ink jet printing heads for directing liquid droplets of ink towards a printing surface.

The apparatus may further include means for applying a cover coating material onto only a part of the surface of the substrate.

According to the invention, there is also provided, a pharmaceutical product comprising a substrate, an active coating layer on a surface of the substrate, the active coating layer comprising biologically active material, and a cover coating layer substantially completely covering the active coating layer.

The pharmaceutical product may further include a second active coating layer, and a cover coating layer substantially completely covering the second active coating layer. In the case of a tablet, for example, the first active coating layer may cover one face of the tablet and the second active coating layer may cover the opposite face of the tablet.

The cover coating layer covering the first active coating layer may be different from the cover coating layer covering the second active coating layer. Thus different release rates of the two active coatings may be obtained as described above.

Advantageously, the coated pharmaceutical product is a solid dosage form, preferably a solid dosage form to be administered orally.

The substrate may contain biologically active material. As indicated above, the method according to the invention is particularly suitable for the case in which the quantity of active component to be administered is low. Where a large quantity of a first active component is to be co-administered with a small quantity of a second active component, the first active component may be present in the substrate, for example the tablet core, in the usual way and the second active component may be contained in a coating on the surface of the substrate in accordance with the present invention.

The active coating layer may cover only a part of the surface area of the substrate. The active coating may cover less than 25% of the surface area of the substrate. Where the substrate is a tablet core, the active coating layer covers less than the total area of a face of the core.

Preferably the area covered by the active coating material layer is less than 20%, more preferably less than 10%. In one preferred embodiment of the invention, the coating material layer is in the form of a spot of material on the surface of the substrate.

The coating layer may be shaped, for example to form a pattern, a picture, symbols, letters or numerals.

The cover coating layer may cover only a part of the surface of the substrate.

The invention also provides a pharmaceutical product made by a method described above.

A further aspect of the invention provides a method of coating a pharmaceutical substrate, the method including the step of applying an active coating material to a surface of the substrate to form a coating layer, the active coating material comprising biological material, in which the active coating layer covers only a part of the surface of the substrate.

It will be understood that the method according to the further aspect of the invention could include a combination of the features described above and may include features of the method described above.

BRIEF DESCRIPTION OF THE DRAWINGS

Embodiments of the invention will now be described by way of example having reference to the drawings of which.

BRIEF DESCRIPTION OF PREFERRED EMBODIMENTS

Figure 1:
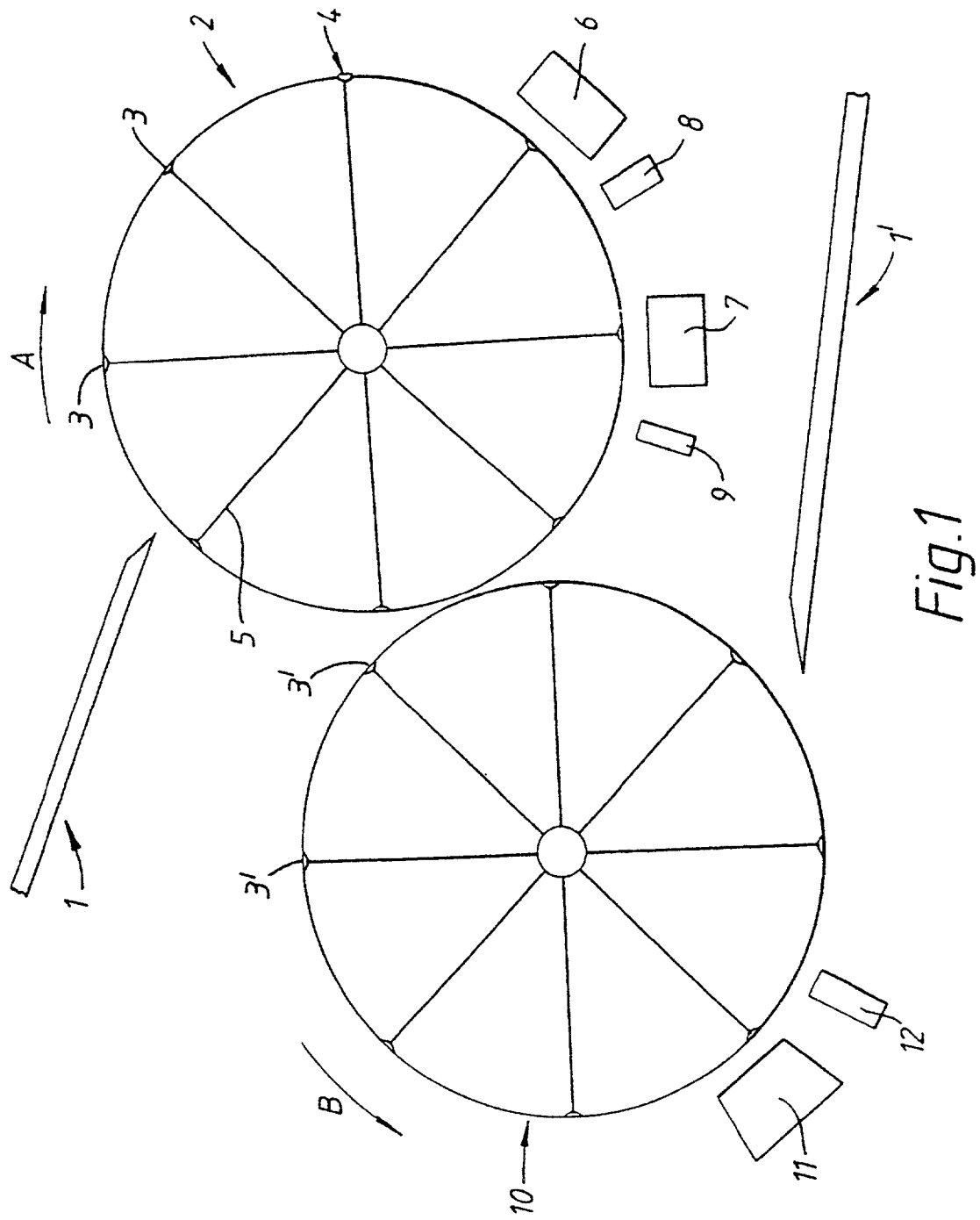
FIG. 1 shows schematically a side view of an apparatus for coating a tablet core in accordance with the invention.

The apparatus shown in FIG. 1 is for coating both faces of pharmaceutical tablet cores. The apparatus comprises an inclined tablet core feed chute 1 leading to a first rotatable wheel 2 having circular depressions 3 in its outer surface. The cores 4 are fed from the chute 1 into the depressions 3 where they are held by suction by means of a suction line 5 in communication with the base of the depression 3 via an opening. The first drum is rotated in the direction shown by the arrow A. Adjacent to the outer surface of the wheel 2 downstream from the feed chute 1 is an active coating station 6 and a cover coating station 7. Downstream from the active coating station is an active coating fusing station 8 at which the active coating is fused and downstream from the cover coating station 7 is a cover coating fusing station 9 at which the cover coating is fused. A cooling station (not shown) may be provided downstream from each of the fusing stations 8, 9 where cool air is directed at the core to cool the fused coating.

A second wheel 10 similar to the first wheel 2 is arranged adjacent to the first wheel 2, the nip between the wheels being downstream of the fusing station 9. The second wheel 10 rotates in an opposite sense to that of the first wheel 2 as shown by the arrow B. Arranged adjacent to the outer edge of the second wheel 10 downstream from the nip of the two wheels are a second cover coating station 11 and a second fusing station 12.

The tablet cores are fed continuously from the core feed chute 1 to the depressions 3 in the rotating wheel 2. The core lies over the opening in the depression 3 leading to the suction line 5 and the core is held in the depression by suction. The core is moved on the rotating wheel 2 to the active coating station 6 where active coating including biologically active material is applied as described in more detail below and is fused at the active coating fusing station 8. The core then moves to the cover coating station 7 where a further coating is applied over the active coating. The coated core then moves to the fusing station 9 where a heater fuses the cover coating to form a film coating secured to the core.

When the core in the depression 3 reaches the nip between the two wheels, the suction holding the core in the depression 3 is released and the core is transferred into a depression 3' on the surface of the rotating second wheel 10 where it is held by suction with coated surfaces of the core adjacent to the surfaces of the depression and the uncoated surfaces of the tablet exposed.

The second wheel 10 moves the core to the second cover coating station 11 and the second fusing station 12 and a second cooling station (not shown) to form a fully coated tablet core.

The core is then moved to an exit chute 1'. The suction holding the core is released and the core drops from the wheel along the chute which takes the cores to be further processed and/or packed.

It will be understood that where only one face of the tablet core is to be coated, the second wheel 10 would be omitted. Further, where an active coating of material including biologically active material is to be coated onto both faces of the tablet, a further active coating station 6' would be positioned by the second wheel upstream from the second cover coating station.

It will be appreciated that the coating material in each of the two cover coating stations may be the same or different materials, and where more than one active coating station is used, the coating material in each of the active coating stations may be the same or different materials.

Figure 2:
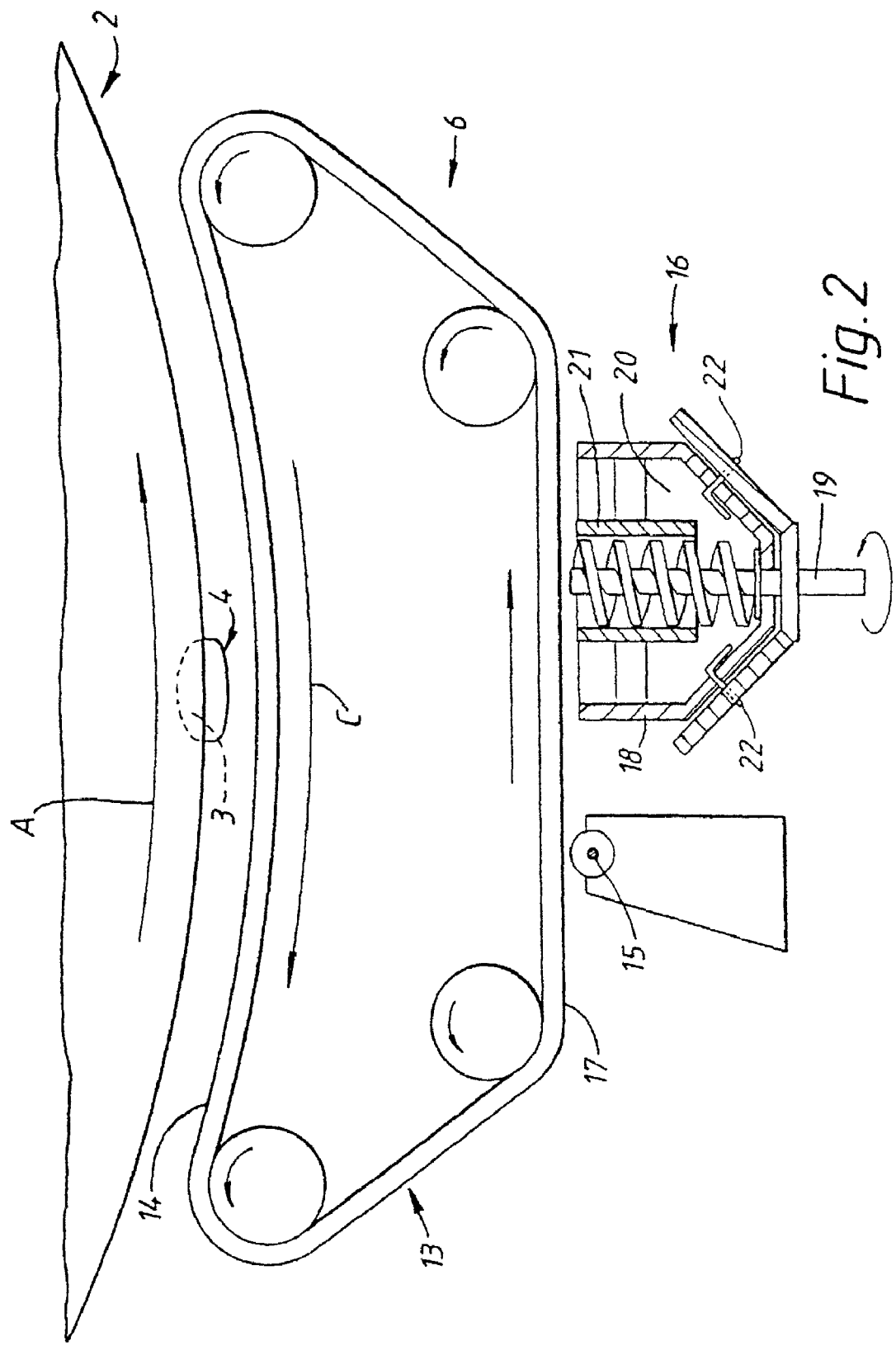
FIG. 2 shows schematically a side view of a part of the apparatus of FIG. 1.

FIG. 2 shows the active coating device 6 in more detail. FIG. 2 shows a portion of the wheel 2 together with a core 4 in a depression 3 on the surface of the wheel 2.

The active coating station 6 comprises a conveyor 13 arranged in a loop in a vertical plane so that the upper surface 14 faces the surface of the wheel and the cores 4 which pass the device 6 as the wheel rotates. The contour of the upper surface 14 of the conveyor 13 is chosen to match the contour of the outer surface of the wheel so that the distance between the core and the upper surface of the conveyor is unchanged as the wheel rotates. The direction of rotation C of the conveyor 13 is such that the direction of movement of the upper surface of the conveyor is opposite to that of the movement of the core over the upper surface of the conveyor. Alternatively, the direction of movement of the upper surface of the conveyor and the core may be the same.

As shown in FIG. 2, a corona charge wire 15 and a powder source 16 are arranged beneath the conveyor immediately below the lower surface 17 of the conveyor.

The corona charge wire 15 sprays charge onto the lower surface 17 of the conveyor. It will be appreciated that a different method could be used to apply charge to the conveyor.

The powder source 16 uses an archimedes screw to form a small mound of powder beneath the lower surface of the conveyor. The source 16 comprises a hopper 18 containing the powder including the biologically active component, and an Archimedes screw 19 which in use passes through the powder material 20 in the hopper 18 and through a vertical barrel 21. Thus, the powder material 20 is circulated from the lower regions of the hopper 18 to the top of the barrel 21 where a moving heap of powder is formed. The heap will be of substantially constant size and shape as excess powder overflows from the top of the barrel 21 and is returned to the hopper 18.

Stirrers 22 are provided in the hopper 18 to help to improve the flow of the powder and break up any agglomerates.

Thus a small moving heap of powder of substantially constant size and shape is formed beneath the lower surface of the conveyor 17.

It will be appreciated that a device other than the Archimedes screw could be used to form the heap of powder.

The powder source 16 is located downstream from the charge spraying device 15 and powder from the heap of powder is attracted to the surface of the charged conveyor 17 where it forms a thin, uniform layer which is transported to the upper surface 14 of the conveyor.

The tablet core 4 passing over the upper surface of the conveyor is held at a different potential from that of the conveyor 13, either by earthing the core or applying a charge to the core as described below, and powder on the conveyor moves from the conveyor to the exposed surfaces of the tablet core 4 to form a powder coating.

The active coating station 6 is enclosed in a housing (not shown) to reduce the risk of powder loss of the active powder. In use the housing has an opening above the upper surface of the conveyor 14 so that the tablet core 4 is exposed to the active powder coating material as it passes the station 6.

It will be appreciated that the thickness of the powder layer formed on the surface of the tablet core depends on several factors including the amount of charge sprayed onto the conveyor, the magnitude of the charge applied to the core, the size of the heap of powder produced, the size of the opening in the housing and the speed of the conveyor. Those factors will be varied to give the desired coating depending on the type of powder and core used.

The tablet core including the active coating then passes to the active coating fusing station 8 which comprises a heater which is used to fuse the coating material. A cooler situated downstream from the active coating fusing station 8 directs air at the core to cool the fused active coating.

The active coated tablet core then passes to the cover coating station 7 where a charge is applied to the tablet core as described below and the core is passed over an earthed trough containing the cover coating powder. The powder from the trough is attracted to the exposed surfaces of the tablet core to form a cover coating over the active coating. The tablet then passes to the cover coating fusing station 9 where the cover coating is fused to form a film coating and to a cooling station where cool air is directed at the core to cool the fused coating.

Figure 3:
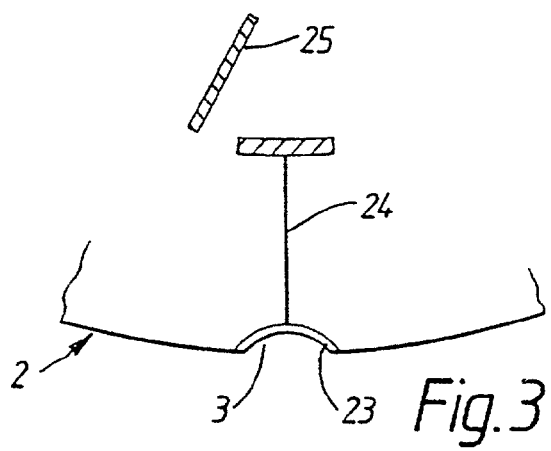
FIG. 3 shows schematically a cross sectional view of part of the apparatus of FIG. 1.

As shown in FIG. 3, where a charge is to be applied to the tablet core at one or more of the coating stations, each depression 3 is electrically insulated from the other depressions on the wheel by means of a cup of insulating material 23 and is provided with a respective pick up arm 24 extending radially inward from the depression 3 towards but ending short of the centre of the wheel. The pick up arms 24 are attached to the inner surface of the wheel 2 and rotate with it. Each associated pick up arm 24 and depression 3 together make a moving electrode which is in contact with the core 4 when it is located in the depression 3.

A stationary electrode 25 is located inside the wheel at each angular position corresponding to each coating station, as required. The outer surfaces of the stationary electrodes are at the same radial distance from the centre of the wheel as the free ends of the pick up arms 24 of the moving electrodes. As the wheel 2 rotates, the moving electrodes contact the stationary electrodes and a charge is applied to the tablet core 4 in the depression 3.

The partially coated tablet core then passes onto the second wheel, and the uncoated surfaces are coated with a cover coating in a similar way.

Figure 4A:
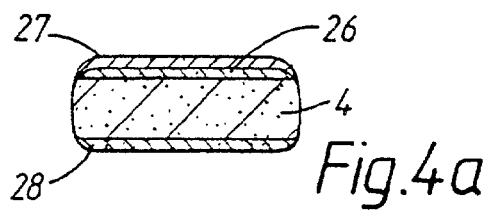
FIGS. 4a to 4c show cross sectional views of tablet cores coated in accordance with the invention.
Figure 4B:
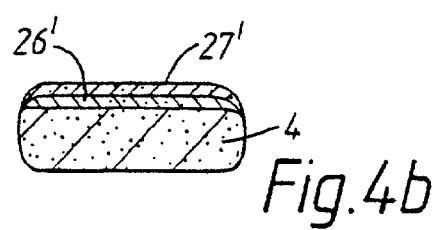

FIGS. 4a and 4b show schematic cross-sectional views of tablets coated in accordance with the first aspect of the present invention. The tablet shown in FIG. 4a comprises a core 4, an active coating layer 26 comprising active material covering the upper surface and part of the side surface of the core, and a cover coating 27 covering the active coating layer 26. The core also has a further cover coating 28 covering the opposite face and part of the side surface of the core. The further cover coating 28 may be of the same or different composition as that of the cover coating 27.

It will be appreciated that the thickness of the coating layers relative to the size of the core have been greatly exaggerated for clarity. For a tablet core of thickness 5 mm, the thickness of each coating layer would usually be of the order of from 5 to 100 µm.

Where the apparatus described above is used to coat the cores, most of the coating material deposited on the core surface will be deposited on the face of the core facing the powder source such that the coating on that face of the core will be thicker than the coating on the exposed side faces of the core where less coating material is deposited.

FIG. 4b shows a tablet having an active coating 26' and a cover coating 27'. The tablet is similar to that of FIG. 4a except that there is no further cover coating on the opposite side of the core.

It will be appreciated that tablets having other combinations of active coatings and cover coatings could be produced. For example, a first coating containing no active material may be applied to all or part of the surfaces of the substrate before the application of the active coating material. For example, where the substrate also includes active material, the first coating may be a delayed release coating.

The composition of the active coating material used will of course depend on the active ingredient to be used and the amount of the coating to be applied.

Active materials most suitable to be applied to the tablet include those materials having a high therapeutic activity, for example those where the usual prescribed dose is about 1mg or less, and which have a good stability to degradation due to heat where the coating material containing active material is to be heated.

An active material which may be applied to a tablet core in accordance with the invention is Diltiazem HCL.

The amount of active ingredient to be coated onto each core or other substrate will generally be small and the active ingredient will usually be diluted with one or more excipients. The excipients used will be chosen so that they aid the coating of the active material onto the cores by, for example improving the electrostatic properties of the powder and its physical properties and aiding the formation of the fused active coating, for example the excipient may be a material which melts at a low temperature to aid the formation of a film.

Where the active coating material is a powder, the particle size will be an important factor with regard to the transfer of the active coating material from the conveyor to the tablet core and to the subsequent fusing of the material. Usually a particle size range of 1 to 200 µm will be used (at least 90% of the particles of the powder having a size within that range).

EXAMPLE

One example of an active coating material is as follows:

| | |
|---|---|
| Xylitol | 45% wt |
| Diltiazem HCL (active) | 45% wt |
| TiO$_2$ | 9% wt |
| Colloidal silica | 1% wt |

It is thought that in at least one embodiment of the invention, the active composition will comprise three main components together with additives.

The components may, for example, comprise the following i) a continuous phase component, for example Xylitol or PEG 6000, ii) the active component, iii) a particle seed and/or charge modifying component, for example TiO$_2$ or silica, iv) a flow aid, for example colloidal silica or magnesium stearate.

Each component may comprise one or more different materials.

The active coating material of the above example was in the form of a powder and had a particle size distribution such that at least 90% wt of the particles had a size in the range of from 5 to 25 µm. It is often preferred that at least 90% by weight of the particles have a size in the range of from 1 to 45 µm. In one preferred embodiment 90% by weight of the particles have a size less than 70 µm, 50% by weight have a particle size less than 40 µm and 10% by weight of the particles have a size less than 10 µm.

The active powder coating material may be produced using one or a combination of the following processing steps:

a) precipitation of two or more of the components to form composite particles
b) spray drying of two or more of the components to form composite particles
c) granulation
d) extrusion
e) micronisation.

For example, all of the components of the composition may be co-micronised to give a powder material having the desired particle size.

An example of a powder cover coating material is as follows:

| | |
|---|---|
| 39.75% | EUDRAGIT (Trade Mark) RS (ammoniomethacrylate copolymer) |
| 39.75% | KLUCEL (Trade Mark) (hydroxyl propyl cellulose) |
| 15.0% | Titanium dioxide |
| 5.0% | Aluminium lake |
| 0.5% | AEROSIL (Trade Mark) 200 (colloidal silicon dioxide) |

The cover coating material was prepared by the following method:

a) A sample containing the % wt of components listed above was premixed in a high shear mixer. Water was added to the mixture in a high shear mixer for a few minutes to give a granulated mixture which was dried in a fluid bed drier at a temperature of about 45° C. for 20 to 30 minutes to give a material having a moisture content (measured as loss on drying) below 3% by weight. The material was impact milled and then micronised using a fluid energy mill to a powder containing particles having a size distribution such that 50% by volume of particles were of a size less than 20 μm.

The cover coating material will usually include components to control the dissolution rate of the cover coating to give controlled release of the active material in the active coating layer. Where more than one active coating is applied to each tablet or other substrate, the release of each active coating can be different where different materials are used for the cover coating over each of those active coatings.

Where one or more of the coatings are applied as liquid coatings, a suitable liquid coating device would be used at the active coating station 6 and/or the cover coating station 7 and the fusing device would be replaced by, for example a drying device to dry the liquid coating, if necessary.

In an alternative embodiment of the invention, an ink jet printer head is used to apply active coating and/or cover coating material in an apparatus similar to that described above and as shown in FIGS. 1 and 3.

The head may be an ink jet printer head, for example an adapted Compact 200 head manufactured by Alphadot Limited. That head has 5 outlets spread over an area of about 10 mm and can be used to direct liquid coating material towards the exposed surfaces of the tablet core such that, for a tablet core having two parallel flat faces, the liquid coating substantially completely covers one of the flat faces.

It will be understood that different types of head may be used to apply coating material to the surface of the substrate and that the head will be chosen so as to give the desired deposition of the coating material on the surface of the substrate to be coated. For example, where the coating is to cover only a part of the exposed surface of the substrate, the size and arrangement of the outlets will be chosen accordingly.

Where, for example, active coating material is to be applied to a tablet core using an ink jet printer head using the apparatus shown in FIGS. 1 and 3, the printer head is arranged at the active coating station 6 and active coating material in the form of a liquid is applied to a surface of a pharmaceutical tablet core held on the first wheel 2. A head for applying the liquid is positioned such that the outlet or outlets of the head is less than 1mm from a surface of a tablet core held on the wheel 2 at the active coating station 6.

The liquid coating material comprises the active component and a solvent, preferably water, and an excipient, for example PEG, to aid in film forming. Preferably the solids content of the liquid coating material is very low, advantageously there would be substantially no solids content and advantageously the active material is fully dissolved in the solvent.

Examples of active liquid coating materials which may be used are as follows

| | | |
|---|---|---|
| a) | Sodium citrate | 0.02 |
| | Chlorpheniramine maleate | 2.48 |
| | Propylene glycol | 4.00 |
| | Water | 18.50 |
| | Ethanol | 75.00 |

| | | |
|---|---|---|
| b) | Sodium citrate | 0.02 |
| | Chlorpheniramine maleate | 2.00 |
| | Methocel E15 | 1.00 |
| | Lactose B.P. | 6.00 |
| | PEG 4000 | 1.00 |
| | Water | 89.98 |

The amounts given above represent percentage by weight of each component.

The apparatus may include heating means 8 downstream from the coating station 6 for drying the applied coating material. However, where the liquid coating material is such that the solvent evaporates quickly, the heater 8 may not be required. It will be appreciated that where the heater 8 is used the temperature required to dry the active coating will be significantly lower than the temperature required to fuse powder coating material as described above.

The apparatus may further include a cover coating station 7 and a fusing station 9 as described above and, where the core is to be further coated, the apparatus includes a second wheel 10 with a coating station 11 and fusing station 12 as described above. Where a further active coating is to be applied, a further active coating station and, optionally, a further heater may be provided upstream from the coating station 11. An example of a suitable cover coating material is described above.

Figure 4C:
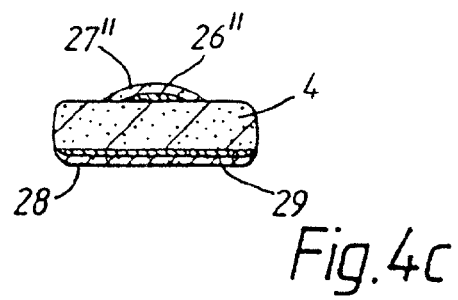

FIG. 4c shows a tablet coated by a method described above. The tablet comprises a core 4, a first active coating layer 26" covering substantially all of the upper face of the core, a cover coating 27" covering the active coating layer and part of the sides of the tablet core, a second active coating layer 29 covering part of the lower surface of the core and a second cover coating layer 28 covering the second active coating layer 29. The two active coating layers 26" and 29 may include the same or different active ingredients; the two cover coating layers 27" and 28 may be of the same or different material and may have different dissolution rates.

Where the active coating material is applied using the method described above, substantially all of the coating material is applied to a face of the tablet core, with substantially no coating material being applied to the sides of the tablet core.

In a further embodiment of the invention, the active coating material is applied to a substrate using an ultrasonic spray head. The ultrasonic spray head forms a cloud of liquid droplets which are charged electrostatically. A charge may be imparted on the droplets, for example, by applying a high voltage to the ultrasonic spray head. The charged droplets become attracted to the substrate which is at a potential difference from the droplets.

It will be appreciated that the apparatus described above could be modified for the coating of pharmaceutical substrates other than conventional tablet cores. As indicated above, the method and apparatus described could be used to coat tablet cores of non-conventional shape or pharmaceutical substrates in the form of a film or sheet.

The invention claimed is:

1. A method of preparing a pharmaceutical dosage unit, the method comprising the steps of:

(a) electrostatically applying an active coating material in the form of a powder from a source to a surface of a pharmaceutical substrate to form an active coating layer, the active coating material comprising biologically active material, and (b) electrostatically applying a cover coating material onto the active coating layer to form a cover coating layer such that the active coating layer is substantially completely covered by the cover coating layer, wherein the coated pharmaceutical substrate is a solid dosage form, and wherein the substrate is supported from above and the powder moves from the source upwards towards a lower surface of the substrate.

2. The method of claim 1, wherein after the active coating material is applied the active coating material is treated to form a fused film coating secured to the substrate.

3. The method of claim 2, wherein the active coating material comprises i) a continuous phase component, ii) the biologically active material, iii) a charge-modifying component, and iv) a flow aid.

4. The method of claim 2, wherein at least 90% by weight of the particles of the active coating material have a particle size in the range of from 5 μm to 25 μm.

5. The method of claim 1, wherein the active coating material is applied to only a part of the surface of the substrate, and the cover coating material covers only a part of the surface of the substrate.

6. The method of claim 1, wherein the cover coating includes biologically active material.

7. The method of claim 1, wherein the method further includes the steps of applying a further coating material which includes biologically active material to a surface of the substrate to form a further coating, the further coating forming a further active coating, and applying a further cover coating material onto the further active coating to form a further cover coating such that the further active coating is substantially completely covered by the further cover coating.

8. The method of claim 7 wherein the biologically active materials are the same and the cover coating materials are different; or the biologically active materials are different.

9. The method according to claim 7 wherein the pharmaceutical substrate is a pharmaceutical tablet core, the first active coating material being applied to one face of a tablet substrate and the further active coating material being applied to the opposite face.

10. The method according to claim 9, wherein the active coating material is in the form of a powder and after the active coating material is applied the active coating material is treated to form a fused film coating secured to the substrate.

11. The method according to claim 2, wherein the method further includes the steps of applying a further coating material which includes biologically active material to the substrate to form a further coating, the further coating forming a further active coating, and applying a further cover coating material onto the further active coating to form a further cover coating such that the further active coating is substantially completely covered by the further cover coating.

12. The method of claim 1, wherein the cover coating material is in the form of a powder and wherein after the cover coating material is applied the cover coating material is treated to form a fused cover film coating secured to the substrate.

13. The method of claim 2, wherein the cover coating material is in the form of a powder and after the cover coating material is applied, the cover coating material is treated to form a fused film coating.

14. The method of claim 6, wherein the cover coating material is in the form of a powder and after the cover coating material is applied, the cover coating material is treated to form a fused film coating.

15. The method of claim 1, wherein the cover coating layer provides delayed release of the biologically active material.

16. The method of claim 6, wherein the biologically active material in the cover coating material is the same as the active material in the active coating layer (a).

17. The method of claim 6, wherein the biologically active material in the cover coating material is different from the active material in the active coating layer (a).

18. The method of claim 1, wherein the method further includes the step of applying a further coating material to form a further coating layer, the further coating material containing biologically active material, the further coating layer forming a further active coating layer.

19. The method of claim 6, wherein the method further includes the step of applying a further coating material to form a further coating layer, the further coating material containing biologically active material, the further coating layer forming a further active coating layer.

20. The method of claim 1, wherein the method comprises supporting the substrate adjacent to the source of the active coating material with a surface of the substrate maintained at such a different electric potential from that of the active coating material that the application of the electric potential causes the active coating material to move from the source of the active coating material towards the substrate, a surface of the substrate becoming coated with the active coating material.

21. The method of claim 2, wherein the method comprises supporting the substrate adjacent to the source of the cover coating material with a surface of the substrate maintained at such a different electric potential from that of the cover coating material that the application of the electric potential causes the cover coating material to move from the source of the cover coating material towards the substrate, a surface of the substrate becoming coated with the cover coating material.

22. The method of claim 13, wherein during the coating with the cover coating material the substrate is supported from above and the powder moves from the source upwards towards a lower surface of the substrate.

23. The method of claim 1, wherein the solid dosage form is a solid dosage form for oral administration.

24. The method of claim 22, wherein the cover coating includes biologically active material.

25. The method of claim 22, wherein the method further includes the step of applying a further coating material to form a further coating layer.

26. The method of claim 22, wherein the method further includes the step of applying a further coating material to form a further coating layer, the further coating material containing biologically active material, the further coating layer forming a further active coating.

27. The method of claim 22, wherein the method further includes the steps of applying a further coating material which includes biologically active material to a surface of the substrate to form a further coating, the further coating forming a further active coating, and applying a further cover coating material onto the further active coating to form a further cover coating such that the further active coating is substantially completely covered by the further cover coating.

28. The method of claim 27, wherein the biologically active materials are the same and the cover coating materials are different; or the biologically active materials are different.

29. The method according to claim 27, wherein the pharmaceutical substrate is a pharmaceutical tablet core, the first active coating material being applied to one face of a tablet substrate and the further active coating material being applied to the opposite face.

30. The method according to claim 29, wherein the active coating material is in the form of a powder and after the active coating material is applied the active coating material is treated to form a fused film coating secured to the substrate.

31. The method of claim 22, wherein at least 90% by weight of the particles of the active coating material have a particle size in the range of from 5 µm to 25 µm.

32. The method according to claim 13, wherein the method further includes the steps of applying a further coating material which includes biologically active material to form a further coating, the further coating forming a further active coating, and applying a further cover coating material onto the further active coating to form a further cover coating such that the further active coating is substantially completely covered by the further cover coating.

33. The method of claim 1, wherein the active coating layer is in the shape of a pattern, a picture, symbols, letters or numerals or is in the form of a spot.

34. The method of claim 1, wherein the substrate is in the form of a tablet core containing active material and the core is coated with delayed release material prior to the application of active material.

35. A method of coating a substrate, the method comprising:
(a) electrostatically applying an active powder material from a source to a surface of the substrate to form an active coating layer, the active coating material comprising biologically active material and treating the active coating material to form an active film coating secured to the substrate, and
(b) electrostatically applying a cover coating material over the active coating layer to substantially completely cover the active coating layer on the surface of the substrate,
wherein the amount of active coating material applied to the substrate is substantially equal to one dose of biologically active material and
wherein the substrate is supported from above and the powder moves from the source upwards towards a lower surface of the substrate.

36. The method of claim 35, wherein the cover coating material is in the form of a powder and after the cover coating material is applied, the cover coating material is treated to form a fused film coating.

37. The method of claim 35, wherein the cover coating layer provides delayed release of the biologically active material.

38. The method of claim 35, wherein the cover coating includes biologically active material.

39. The method of claim 35, wherein the coated substrate is a solid dosage form for oral administration.

40. The method of claim 38, wherein the cover coating material is in the form of a powder and after the cover coating material is applied the cover coating material is treated to form a fused film coating.

41. The method of claim 35, wherein the active coating layer is in the shape of a pattern, a picture, symbols, letters or numerals or is in the form of a spot.

42. The method of claim 35, wherein the substrate is in the form of a tablet core containing active material and the core is coated with delayed release material prior to the application of active material.

43. A method of coating a pharmaceutical substrate, the method comprising the steps of:
(a) applying an active coating material to a surface of the substrate to form an active coating layer, the active coating material comprising biologically active material, and
(b) electrostatically applying a cover coating material in the form of a powder from a source onto the active coating layer to form a cover coating layer such that the active coating layer is substantially completely covered by the cover coating layer,
wherein the coated pharmaceutical substrate is a solid dosage form, and
wherein during the coating with the cover coating material the substrate is supported from above and the powder moves from the source upwards towards a lower surface of the substrate.

44. The method of claim 43, wherein the cover coating includes biologically active material.

45. The method of claim 43, wherein the method further includes the steps of applying a further coating material which includes biologically active material to a surface of the substrate to form a further coating, the further coating forming a further active coating, and applying a further cover coating material onto the further active coating to form a further cover coating such that the further active coating is substantially completely covered by the further cover coating.

46. The method of claim 45, wherein the biologically active materials are the same and the cover coating materials are different; or the biologically active materials are different.

47. The method of claim 45, wherein the pharmaceutical substrate is a pharmaceutical tablet core, the first active coating material being applied to one face of a tablet substrate and the further active coating material being applied to the opposite face.

48. The method according to claim 43, wherein after the cover coating material is applied the cover coating material is treated to form a fused cover film coating secured to the substrate.

49. The method of claim 48, wherein the method further includes the steps of applying a further coating material which includes biologically active material to form a further coating, the further coating forming a further active coating, and applying a further cover coating material onto the further active coating to form a further cover coating such that the further active coating is substantially completely covered by the further cover coating.

50. The method of claim 43, wherein the active coating material comprises:
   i) a continuous phase component,
   ii) the biologically active material,
   iii) a charge-modifying component, and
   iv) a flow aid.

51. The method of claim 43, wherein the active coating material is applied to only a part of the surface of the substrate, and the cover coating material covers only a part of the surface of the substrate.

52. The method of claim 44, wherein after the cover coating material is applied, the cover coating material is treated to form a fused film coating.

53. The method of claim 43, wherein the cover coating layer provides delayed release of the biologically active material.

54. The method of claim 44, wherein the biologically active material in the cover coating material is the same as the active material in the active coating layer (a).

55. The method of claim 44, wherein the biologically active material in the cover coating material is different from the active material in the coating layer (a).

56. The method of claim 43, wherein the method further includes the step of applying a further coating material to form a further coating layer.

57. The method of claim 44, wherein the method further includes the step of applying a further coating material to form a further coating layer.

58. The method of claim 43, wherein the method further includes the step of applying a further coating material to form a further coating layer, the further coating material containing biologically active material, the further coating layer forming a further active coating layer.

59. The method of claim 44, wherein the method further includes the step of applying a further coating material to form a further coating layer, the further coating material containing biologically active material, the further coating layer forming a further active coating layer.

60. The method of claim 43, wherein the method comprises supporting the substrate adjacent to the source of the cover coating material with a surface of the substrate maintained at such a different electric potential from that of the cover coating material that the application of the electric potential causes the cover coating material to move from the source of the cover coating material towards the substrate, a surface of the substrate becoming coated with the cover coating material.

61. The method of claim 43, wherein the solid dosage form is a solid dosage form for oral administration.

62. The method of claim 43, wherein the active coating material is in the form of a powder and after the active coating material is applied the active coating material is treated to form a fused film coating secured to the substrate.

63. The method of claim 44, wherein the method further includes the step of applying a further coating material to form a further coating layer.

64. The method of claim 43, wherein the active coating layer is in the shape of a pattern, a picture, symbols, letters or numerals or is in the form of a spot.

65. The method of claim 43, wherein the substrate is in the form of a tablet core containing active material and the core is coated with delayed release material prior to the application of active material.

* * * * *